United States Patent
Tanaka et al.

(10) Patent No.: US 12,053,367 B2
(45) Date of Patent: Aug. 6, 2024

(54) PLAIN-WEAVE FABRIC, METHOD FOR MANUFACTURING SAME, AND STENT GRAFT

(71) Applicant: Toray Industries, Inc., Tokyo (JP)

(72) Inventors: Nobuaki Tanaka, Osaka (JP); Hiroshi Tsuchikura, Otsu (JP); So Kakiyama, Otsu (JP); Kazuhiro Tanahashi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 1039 days.

(21) Appl. No.: 16/963,906

(22) PCT Filed: Jan. 15, 2019

(86) PCT No.: PCT/JP2019/000947
§ 371 (c)(1),
(2) Date: Jul. 22, 2020

(87) PCT Pub. No.: WO2019/150937
PCT Pub. Date: Aug. 8, 2019

(65) Prior Publication Data
US 2021/0038364 A1   Feb. 11, 2021

(30) Foreign Application Priority Data

Jan. 30, 2018 (JP) ................... 2018-013292
Aug. 9, 2018 (JP) ................... 2018-150426

(51) Int. Cl.
*A61F 2/07* (2013.01)
*D03D 1/00* (2006.01)
(Continued)

(52) U.S. Cl.
CPC ............... *A61F 2/07* (2013.01); *D03D 1/00* (2013.01); *D03D 13/004* (2013.01);
(Continued)

(58) Field of Classification Search
None
See application file for complete search history.

(56) References Cited

U.S. PATENT DOCUMENTS

| | | |
|---|---|---|
| 5,532,311 A | 7/1996 | Sirvio et al. |
| 6,461,665 B1 | 10/2002 | Scholander |

(Continued)

FOREIGN PATENT DOCUMENTS

| | | |
|---|---|---|
| CA | 2825305 C | 8/2015 |
| CN | 1178174 A | 4/1998 |

(Continued)

OTHER PUBLICATIONS

JPH10292244 English Machine Translation. 1998. (Year: 1998).*

(Continued)

*Primary Examiner* — Jenna L Johnson
(74) *Attorney, Agent, or Firm* — Buchanan Ingersoll & Rooney PC

(57) ABSTRACT

There is provided a plain-weave fabric excellent in low air permeability and waterproofness. Further, there is provided a stent graft excellent in low water permeability mechanical properties and catheter storage capacity, including the plain-weave fabric as a graft substrate. A plain-weave fabric woven by interlacing weaving yarns in warp and weft, in which weaving yarns YA and YB arranged in the same direction have different crimp ratios A and B, respectively, a relationship thereof satisfies Formula 1, and the crimp ratio B is 4% or more, and the plain-weave fabric is preferably used for a stent graft; A≥B×1.2.

16 Claims, 3 Drawing Sheets

(51) Int. Cl.

| | | |
|---|---|---|
| *D03D 13/00* | (2006.01) | |
| *D03D 15/283* | (2021.01) | |
| *D06C 15/00* | (2006.01) | |
| *D06M 15/277* | (2006.01) | |
| *D06M 15/643* | (2006.01) | |

(52) U.S. Cl.
CPC .......... *D03D 15/283* (2021.01); *D06C 15/00* (2013.01); *D06M 15/277* (2013.01); *D06M 15/643* (2013.01); *A61F 2250/0076* (2013.01); *D10B 2401/02* (2013.01); *D10B 2401/06* (2013.01); *D10B 2509/06* (2013.01)

(56) References Cited

U.S. PATENT DOCUMENTS

| | | |
|---|---|---|
| 8,263,504 B2 | 9/2012 | Bouillon et al. |
| 8,426,326 B2 | 4/2013 | Bouillon et al. |
| 9,795,721 B2 | 10/2017 | Kadowaki |
| 9,822,471 B2 | 11/2017 | Ise |
| 10,806,562 B2 | 10/2020 | Takahashi et al. |
| 2004/0213818 A1 | 10/2004 | Kashiwabara et al. |
| 2006/0009835 A1 | 1/2006 | Osborne et al. |
| 2010/0094390 A1 | 4/2010 | Goldmann et al. |
| 2013/0041452 A1 | 2/2013 | Fujita et al. |
| 2015/0329998 A1 | 11/2015 | Ise |
| 2018/0147044 A1 | 5/2018 | Tsuchikura et al. |
| 2018/0208147 A1 | 7/2018 | Yokoi |
| 2019/0015192 A1 | 1/2019 | Nakazawa et al. |

FOREIGN PATENT DOCUMENTS

| | | | |
|---|---|---|---|
| CN | 103932819 A | | 7/2014 |
| CN | 104870703 A | | 8/2015 |
| CN | 105421077 A | | 3/2016 |
| CN | 106012230 A | | 10/2016 |
| EP | 3406224 A1 | | 11/2018 |
| JP | 6041947 B2 | | 9/1985 |
| JP | 6047287 B2 | | 10/1985 |
| JP | H05-208045 A | | 8/1993 |
| JP | 10151192 A | | 6/1998 |
| JP | 10245741 A | | 9/1998 |
| JP | 10292244 A | * | 11/1998 |
| JP | 10292244 A | | 11/1998 |
| JP | 10513074 A | | 12/1998 |
| JP | 2000225198 A | | 8/2000 |
| JP | 2002363835 A | | 12/2002 |
| JP | 3497612 B2 | | 2/2004 |
| JP | 2007138357 A | | 6/2007 |
| JP | 2008505713 A | | 2/2008 |
| JP | 4152075 B2 | | 9/2008 |
| JP | 4273965 B2 | | 6/2009 |
| JP | 2010-512867 A | | 4/2010 |
| JP | 2015017356 A | | 1/2015 |
| JP | 2016014204 A | | 1/2016 |
| JP | 2016123764 A | | 7/2016 |
| JP | WO2016159264 A1 | | 11/2017 |
| RU | 9614 U1 | | 4/1999 |
| RU | 2427675 C2 | | 8/2011 |
| WO | 2007148018 A1 | | 12/2007 |
| WO | 2011136243 A1 | | 11/2011 |
| WO | 2015080177 A1 | | 6/2015 |
| WO | 2016190202 A1 | | 12/2016 |
| WO | 2017010458 A1 | | 1/2017 |
| WO | 2017126009 A1 | | 7/2017 |

OTHER PUBLICATIONS

JP 4310526 English Machine Translation. 2009. (Year: 2009).*
Chinese Office Action for Chinese Application No. 201980009968. 1, dated Apr. 24, 2022 with translation, 14 pages.
Indian Examination Report for Indian Application No. 202047034272, dated Mar. 7, 2022 with translation, 6 pages.
International Search Report and Written Opinion for International Application No. PCT/JP2019/000947, dated Mar. 5, 2019, 6 pages.
Chinese Office Action for Chinese Application No. 2019800099681, dated Oct. 9, 2021 with translation, 20 pages.
Extended European Search Report for European Application No. 19746867.1, dated Oct. 22, 2021, 10 pages.
Russian Office Action with Search Report for Russian Application No. 2020128014, dated Nov. 23, 2021, with translation, 20 pages.
Chinese Office Action for Chinese Application No. 201980009968. 1, dated Mar. 24, 2021 with translation, 24 pages.
Office Action (Notice of Reasons for Refusal) issued Jun. 21, 2022, by the Japan Patent Office in corresponding Japanese Patent Application No. 2019-140537 and an English translation of the Office Action. (7 pages).

* cited by examiner

PLAIN-WEAVE FABRIC, METHOD FOR MANUFACTURING SAME, AND STENT GRAFT

CROSS REFERENCE TO RELATED APPLICATIONS

This is the U.S. National Phase Application of PCT/JP2019/000947, filed Jan. 15, 2019, which claims priority to Japanese Patent Application No. 2018-013292, filed Jan. 30, 2018 and Japanese Patent Application No. 2018-150426, filed Aug. 9, 2018, the disclosures of each of these applications being incorporated herein by reference in their entireties for all purposes.

FIELD OF THE INVENTION

The present invention relates to a plain-weave fabric excellent in low air permeability and waterproofness. In addition, the present invention relates to a stent graft including the plain-weave fabric that is thin and also excellent in mechanical properties and low water permeability as a graft substrate.

BACKGROUND OF THE INVENTION

As a woven fabric excellent in low air permeability and waterproofness, resin coated products such as polyurethane and the like are widely used for sports clothing and the like.

However, although a woven fabric such as a resin coated product is very excellent in low air permeability and waterproofness, it has a defect that it is poor in soft feeling, and thus, a high-density woven fabric having soft texture is strongly required.

In order to meet such requirement, various studies have been made such as reducing single yarn fineness of constituent fiber yarns and weaving at a high density.

For example, Patent Document 1 discloses a technique capable of providing a high-density woven fabric made of polyester filament yarns, that is a non-coated type thin woven fabric, has high waterproof performance, soft texture, a tear strength the level of which does not cause any practical problem, and is well-tailored after the fabric is sewn up, in which a high-density woven fabric using a polyester filament yarn having a single yarn fineness of fiber yarns constituting a woven fabric of 0.6 denier or less and a total fineness of 60 to 120 denier, a warp yarn is made of a crimped yarn, and the total fineness of the warp yarn, the total fineness of the weft yarn and the warp yarn cover factor satisfy a predetermined relational expression.

Such woven fabrics have also been applied to stent grafts used to treat aneurysms.

An aneurysm is an abnormal dilation of the arterial wall, and when left untreated, the aneurysm may rupture and cause fatal major bleeding. It is an advantage that major bleeding due to the rupture can be avoided and the patient's stay in the hospital and ICU can be shortened by delivering a stent graft to the aorta and placing it in the affected area using a catheter, before the aneurysm ruptures.

The stent graft is inserted from the artery of the femur or the like, but the diameter of the catheter is large, typically about 18 French (Fr) (3 Fr=1 mm), so it cannot be said that the degree of invasiveness is low at present and patients with thin blood vessels, such as elderly patients and women, are out of the range of application due to the difficulty in inserting a stent graft, thus many patients still do not benefit from this treatment. Moreover, even if the stent graft is used, it is thick and thus painful. Therefore, it is necessary to design a stent graft that can be stored in a catheter having a smaller diameter, and thus it has been devised to make the stent and the cloth thinner and more flexible when folded so that they can be inserted even through a thin blood vessel as much as possible. These devises have been studied so as to be compatible with low blood leakage, that is, low water permeability, in which a stent graft should originally have.

As an improvement in the graft base cloth used for the stent graft, it is considered that the conventional cloth is made thinner, but when it is simply made thin, there are problems that the strength of the cloth is lowered and the water permeability is increased. Therefore, there is disclosed a base cloth in which naps of ultrafine fibers are formed on the surface, and the thickness is 0.2 mm or less when the base cloth is compressed during insertion, and 0.4 mm or more after being placed in a blood vessel (Patent Document 2). In addition, there is also a technique for forming a thin structure by using 5 to 40 denier yarns to constitute a woven fabric or the like (Patent Document 3). Further, it is disclosed that a high-density woven fabric is calendered to apply a base cloth that is thin but has low water permeability to a stent graft (Patent Document 4).

Patent Documents

Patent Document 1: Japanese Patent Laid-open Publication No. H10-245741
Patent Document 2: Japanese Patent Laid-open Publication No. 2000-225198
Patent Document 3: Japanese Translation of PCT International Application Publication No. 2008-505713
Patent Document 4: WO 2011/0136243 A

SUMMARY OF THE INVENTION

However, the high-density woven fabric described in Patent Document 1 could not be said to have a sufficiently high cover factor to obtain a sufficient level of low air permeability, and was not satisfactory.

As described in Patent Document 2, when nap raising a base cloth made of ultrafine fibers, although some improvement in mechanical strength could be achieved because entanglement of fibers increases, substantial fiber density did not increase. Therefore, it was difficult to drastically improve low water permeability and mechanical strength.

On the other hand, the use of fine yarn as described in Patent Document 3 was effective for producing a thin base material, but it was difficult to achieve both low water permeability and flexibility. Specifically, when the distance between the yarns is made small in order to make the yarns thin and reduce the water permeability, it is inevitably increased in weaving density, and eventually the thickness is increased. On the contrary, when the fineness is reduced while suppressing the weaving density below a certain level, the strength is decreased and the water permeability is increased. Therefore, no means for satisfying all of thinness, high strength, low water permeability and flexibility has been found.

Patent Document 4 discloses a calendered base cloth having a cover factor of 1300 to 4000 using ultrafine fibers having a single yarn fineness of 0.1 to 2.0 dTex. Although the base cloth satisfies thickness and low water permeability, there is a limit on mechanical properties obtained by weaving uncrimped fibers, and a sufficient strength of 200 N/cm or more that can withstand manual operation and biological movement and pulsation is not satisfied.

A first object of the present invention is to provide a plain-weave fabric improved in the problems of the prior art and excellent in low air permeability and waterproofness.

Further, a second object of the present invention is to provide a plain-weave fabric that is thin and also excellent mechanical properties and water permeability and can be also applied to medical applications that were difficult to apply in the prior art, and a stent graft including the plain-weave fabric as a graft substrate.

In order to solve such a problem, the present invention according to exemplary embodiments has the following configurations.

(1) A plain-weave fabric woven by interlacing weaving yarns in warp and weft, wherein weaving yarns YA and YB arranged in the same direction have different crimp ratios A and B, respectively, a relationship thereof satisfies Formula 1, and the crimp ratio B is 4% or more.

$$A \geq B \times 1.2 \quad \text{(Formula 1)}$$

(2) The plain-weave fabric according to (1), wherein the crimp ratio A is 15% or more.

(3) The plain-weave fabric according to (1) or (2), wherein the weaving yarn YA having the crimp ratio A and the weaving yarn YB having the crimp ratio B are arranged at a ratio of 1:1.

(4) The plain-weave fabric according to any one of (1) to (3), having a cover factor of 2400 or more.

(5) The plain-weave fabric according to any one of (1) to (4), having an air permeability of 0.1 $cm^3/cm^2 \cdot sec$ or less.

(6) The plain-weave fabric according to any one of (1) to (5), having a water pressure resistance of 9.8 kPa (1000 mm $H_2O$) or more.

(7) The plain-weave fabric according to any one of (1) to (6), wherein at least one surface is calendered.

(8) The plain-weave fabric according to any one of (1) to (7), wherein at least one surface is subjected to water repellent finishing.

(9) The plain-weave fabric according to any one of (1) to (8), wherein the weaving yarns YA and YB arranged in the same direction have different hot-water dimensional change rates a and b, respectively, and are weaving yarns woven using raw yarns Ya and Yb in which a relationship thereof satisfies Formula 2.

$$b \geq a \times 1.1 \quad \text{(Formula 2)}$$

(10) The plain-weave fabric according to any one of (1) to (9), having a tensile strength at break in the warp direction of 200 N/cm or more.

(11) The plain-weave fabric according to any one of (1) to (10), having a tensile elongation at break in the warp direction of 40% or more and 55% or less.

(12) The plain-weave fabric according to any one of (1) to (11), having a tensile modulus in the warp direction of 300 Pa or more.

(13) The plain-weave fabric according to any one of (1) to (12), having a water permeability rate of 70 mL/min/$cm^2$ or less.

(14) The plain-weave fabric according to any one of (1) to (13), which is used for a prosthesis.

(15) The plain-weave fabric according to any one of (1) to (13), which is used for a stent graft.

(16) The method for producing a plain-weave fabric according to any one of (1) to (15), wherein the fabric is woven under the following conditions (i) and/or (ii):

(i) the raw yarns Ya and Yb having different hot-water dimensional change rates are used to be arranged in the same direction and woven;

(ii) when weaving, the weaving yarns YA and YB arranged in the same direction are woven at different tensions.

(17) A stent graft including the plain-weave fabric according to any one of (1) to (15) as a graft substrate.

(18) The stent graft according to claim 17, which carries heparin, a heparin derivative, or a low molecular weight heparin.

According to the present invention, it is possible to provide a plain-weave fabric excellent in low air permeability and waterproofness.

Furthermore, it is possible to provide a plain-weave fabric that is thin enough to be able to be stored in a thin catheter and also excellent mechanical properties and water permeability, and can be applied to a prosthesis such as a stent graft having properties that were impossible in the prior art, and also a stent graft including the plain-weave fabric as a graft substrate.

DETAILED DESCRIPTION OF EMBODIMENTS OF THE INVENTION

Figure 1:
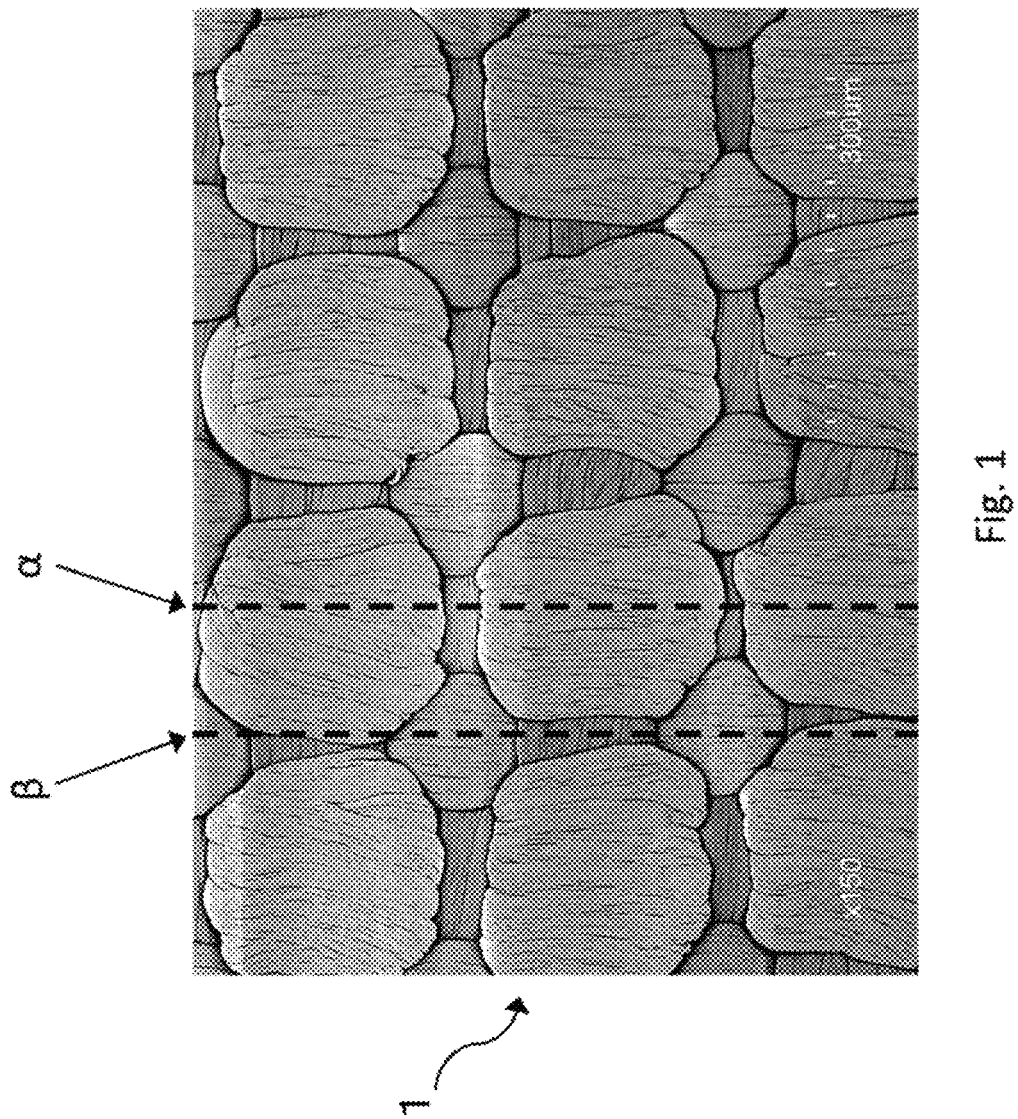
FIG. 1 is a surface SEM photograph of a plain-weave fabric obtained in Example 4.

The plain-weave fabric according to embodiments of the present invention is a plain-weave fabric woven by interlacing weaving yarns in warp and weft, in which weaving yarns YA and YB arranged in the same direction have different crimp ratios A and B, respectively, the relationship thereof satisfies Formula 1. Moreover, the crimp ratio B is 4% or more.

$$A \geq B \times 1.2 \quad \text{(Formula 1)}$$

It should be noted that the above phrase "weaving yarns arranged in the same direction have different crimp ratios, respectively" means that when a certain weaving yarn arranged in the warp direction and/or the weft direction has a certain crimp ratio, at least one kind or more of weaving yarns having a crimp ratio at least different from the crimp ratio are present arranged in the same direction as the weaving yarn. Then, of the two or more types of crimp ratios, the maximum one is taken as the "crimp ratio A", and the minimum one is taken as the "crimp ratio B", and the weaving yarn having the "crimp ratio A" is taken as the "weaving yarn YA", and the weaving yarn having the "crimp ratio B" is taken as the "weaving yarn YB".

The relationship between the crimp ratios A and B is preferably "$A \geq B \times 1.2$", further preferably "$A \geq B \times 1.5$", and more preferably "$A \geq B \times 2$". The upper limit of A is preferably "$A \leq B \times 35$", and more preferably "$A \leq B \times 30$".

The crimp ratio B is preferably 4% or more, and more preferably 5% or more. The upper limit is preferably 15% or less.

Further, the crimp ratio A is preferably 15% or more, and more preferably 30% or more. The upper limit is preferably 200% or less.

By setting the relationship between the crimp ratios A and B in the above ranges, an extremely high density plain-weave fabric can be obtained. Further, when the woven plain-weave fabric is calendered, a yarn having a high crimp ratio is compressed and spread so that a woven fabric interlacing point is covered, and a thin woven fabric with low air permeability can also be obtained.

In the woven fabric, it is preferable that the weaving yarn YA having the crimp ratio A and the weaving yarn YB having the crimp ratio B are arranged at a ratio of 1:1.

The "ratio" of the weaving yarn having the crimp ratio A and the weaving yarn having the crimp ratio B means the number ratio of weaving yarns. The number of weaving yarns is calculated by taking a unit where a warp or weft yarn interlaces with a weft or warp yarn as one, and is counted as one when inserting a plurality of yarns at the same port. The phrase "the weaving yarn YA and the weaving yarn YB having the crimp ratio B are arranged at a ratio of 1:1" means that the same numbers of the weaving yarns YA and the weaving yarns YB are alternately arranged.

Among them, it is preferable that the weaving yarn having the crimp ratio A and the weaving yarn having the crimp ratio B are alternately arranged every one yarn or two yarns.

With the above configuration, a woven fabric that is durable and has excellent dimensional stability can be obtained.

Further, weaving yarns YA and YB arranged in the same direction have different crimp ratios A and B, whereby it is possible to obtain a high-level high-density woven fabric which has not been obtained conventionally. The cover factor is preferably 2400 or more, further preferably 2500 or more, and more preferably 2600 or more. The upper limit is preferably 4000 or less.

The cover factor (Cf) is calculated by the following equation.

$$Cf = N_W \times (D_W)^{1/2} + N_F \times (D_F)^{1/2}$$

$N_W$: Weaving density of warp yarns (yarns/2.54 cm)
$N_F$: Weaving density of weft yarns (yarns/2.54 cm)
$D_W$: Total fineness of warp yarns (dtex)
$D_F$: Total fineness of weft yarns (dtex)

By setting the cover factor in the above ranges, a woven fabric that is lightweight and thin and has low air permeability is obtained. When the woven fabric has a cover factor of less than 2400, a thin and light woven fabric can be obtained, but the non-coated type is difficult to satisfy the low air permeability. On the other hand, when it exceeds 4000, although the low air permeability is satisfied, the woven fabric tends to be heavy.

Further, in a preferred embodiment of the present invention, it is possible to achieve an air permeability of 0.1 $cm^3/cm^2 \cdot sec$ or less, and it is also possible to achieve 0.08 $cm^3/cm^2 \cdot sec$ or less in a further preferred embodiment, and 0.06 $cm^3/cm^2 \cdot sec$ or less in a more preferred embodiment. The lower limit is practically about 0.01 $cm^3/cm^2 \cdot sec$ or more.

By setting the air permeability in the above ranges, it is possible to suppress batting and down omission when used in a down jacket, for example.

Further, in a preferred embodiment of the present invention, it is possible to achieve a water pressure resistance of 9.8 kPa (1000 mm $H_2O$) or more, and it is also possible to achieve 19.6 kPa (2000 mm $H_2O$) or more in a further preferred embodiment, and 29.4 kPa (3000 mm $H_2O$) or more in a more preferred embodiment. The upper limit is usually preferably 86.6 kPa (7000 mm $H_2O$) or less.

By setting the water pressure resistance in the above ranges, a woven fabric that is not submerged is obtained. When it is less than 9.8 kPa (1000 mm $H_2O$), for example, when used in a windbreaker, water resistance to wind and rain is insufficient, and rain seeps into the clothes. However, in order to exceed 86.8 kPa (7000 mm $H_2O$), it may be necessary to devise a film processing of polyurethane resin or the like, and when a large amount of resin is required for film processing, the lightness may be impaired. Even when it is used for a stent graft, if it is less than 9.8 kPa (1000 mm $H_2O$), the water permeability is insufficient and water will seep into it. in order to exceed 86.8 kPa (7000 mm $H_2O$), a polymer coating may be applied to impart water resistance, but the polymer coated layer increases the thickness and hinders catheter storage capacity.

When used for medical applications, for example, in the case of a stent graft, it is stored in a catheter and delivered to the affected area. On the other hand, mechanical properties that withstand the movement of a living body for a long period of time and properties that do not leak blood are required. When the woven fabric is too thick, it cannot be stored in the catheter, and when it is too thin, it lacks long-term mechanical durability, and when the cover factor is low, it causes blood leakage. When the cover factor is 2400 or more and 4000 or less, the thickness is thin enough to be stored in the catheter, and blood leakage can be also prevented. By weaving fine fibers at a high density, a woven fabric member that is thin and excellent in mechanical properties and blood leakage resistance can be obtained.

When the breaking strength is too weak, it tends to be unable to follow the movement in the living body and break easily in the blood vessel, but in a preferred embodiment of the present invention, it is also possible to achieve a tensile strength at break of 200 N/cm or more in the warp direction, and it is also possible to achieve 220 N or more in a further preferred embodiment. The upper limit is practically 500 N/cm or less.

Further, when the elongation at break is too weak, it tends to break when the catheter is stored, but in a preferred embodiment of the present invention, it is possible to achieve a tensile elongation at break of 40% or more in the warp direction, and it is also possible to achieve 45% or more in a further preferred embodiment. The upper limit is practically 55% or less. Furthermore, it is possible to achieve a tensile modulus of 300 Pa or more, and it is also possible to achieve 400 Pa or more in a further preferred embodiment.

In a preferred embodiment of the present invention, the water permeability rate can be set to 70 mL/min/$cm^2$ or less, and it can be set to 20 mL/min/$cm^2$ or less in a further preferred embodiment. The lower limit is practically about 0.01 mL/min/$cm^2$.

The plain-weave fabric of the present invention is preferably composed of multifilament yarns. As the fibers forming the multifilament yarn, for example, polyamide fibers, polyester fibers, aramid fibers, rayon fibers, polysulfone fibers, ultra high molecular weight polyethylene fibers, polyolefin fibers, and the like can be used. Among them, polyamide fibers and polyester fibers, which are excellent in mass productivity and economic efficiency, are preferable.

Examples of the polyamide fiber include fibers made of Nylon 6, Nylon 66, Nylon 12, Nylon 46, a copolymerized polyamide of Nylon 6 and Nylon 66, copolymerized polyamides obtained by copolymerizing Nylon 6 with polyalkylene glycol, dicarboxylic acid, amine, or the like. Nylon 6 fiber and Nylon 66 fiber are particularly preferable because they have excellent impact resistance.

In addition, examples of the polyester fiber include fibers made of polyethylene terephthalate, polybutylene terephthalate, or the like. The polyester fiber may also be a fiber made of a copolymerized polyester obtained by copolymerizing polyethylene terephthalate or polybutylene terephthalate with an aliphatic dicarboxylic acid, such as isophthalic acid, 5-sodium sulfoisophthalate or adipic acid as an acid component.

It is also preferable that the fibers constituting the multifilament yarn contain a heat stabilizer, an antioxidant, a light stabilizer, a smoothing agent, an antistatic agent, a plasticizer, a thickener, a pigment, a flame retardant, and the like.

The materials of the warp and weft yarns may be the same or different, but it is preferable to use the same material in consideration of post-processing and dyeing.

The multifilament yarn preferably used in the plain-weave fabric of the present invention preferably has a total fineness of 22 to 220 dtex, and preferably 33 to 167 dtex. By setting the total fineness of the multifilament yarns within the above ranges, it is easy to obtain sufficient strength as a thin plain-weave fabric and it is easy to obtain a light woven fabric.

The single fiber fineness of the multifilament yarn is preferably 0.01 dtex to 18 dtex, and preferably 0.02 dtex to 10 dtex, from the viewpoint of woven fabric flexibility. Further, the multifilament yarns constituting the plain-weave fabric may be a multifilament yarn obtained by direct spinning, or may be a so-called ultrafine fiber obtained by subjecting sea-island composite fibers to sea removal treatment.

The plain-weave fabric of the present invention can be produced, for example, as follows.

Examples of a method for giving a crimp ratio difference to the yarns arranged in the same direction include a method of using raw yarns having different hot-water dimensional change rates, a method of weaving the weaving yarns YA and YB arranged in the same direction at different tensions during weaving, and the like.

Examples of the method of using raw yarns having different hot-water dimensional change rates preferably include the following method.

That is, at the time of weaving, it is a method of using raw yarns having different hot-water dimensional change rates a and b as the raw yarns Ya and Yb arranged in the same direction, and there is no limitation as long as each hot-water dimensional change rate is a desired crimp ratio, but it is preferable to select the raw yarns Ya and Yb, a relationship thereof satisfies Formula 2.

$$b \geq a \times 1.1 \quad \text{(Formula 2)}$$

In addition, the above phrase "having different hot-water dimensional change rates as the raw yarns arranged in the same direction" means that when certain raw yarns used for the weaving yarns arranged in the warp direction and/or the weft direction have a certain hot-water dimensional change rate, it is used for weaving yarns arranged in the same direction as the weaving yarns using the raw yarns having a hot-water dimensional change rate different from at least the hot-water dimensional change rate. That is, for example, in the warp direction, two or more types of raw yarns Ya and Yb having different hot-water dimensional change rates are arranged in the same direction as warp yarns and woven. In the weft direction, two or more types of raw yarns having different hot-water dimensional change rates a and b are arranged as weft yarns and woven.

Then, of the two or more types of hot-water dimensional change rates, the maximum one is taken as the "hot-water dimensional change rate b", and the minimum one is taken as the "hot-water dimensional change rate a".

The relationship between the hot-water dimensional change rates a and b is preferably "$b \geq a \times 1.1$", further preferably "$b \geq a \times 1.5$", and more preferably "$b \geq a \times 3$". The upper limit of b is preferably "$b \leq a \times 30$".

These conditions are appropriately selected so that the crimp ratio of the plain-weave fabric is controlled in the range specified in the present invention.

It is preferable that the raw yarn Ya having the hot-water dimensional change rate a and the raw yarn Yb having the hot-water dimensional change rate b are alternately arranged every one yarn or two yarns. By subjecting the woven fabric using the above raw yarns to hot water treatment, the yarn having a smaller hot-water dimensional change rate is raised on the surface, and the crimp ratio of the yarns arranged in the same direction can be made different.

In addition, an raw yarn in which the hot-water dimensional change rate largely changes has a relatively large diameter when subjected to hot water treatment. When using an raw yarn with a large hot-water dimensional change rate as a weaving yarn, in consideration of the fact that the diameter becomes thicker, the weaving density is adjusted so as not to be too large and the fineness is adjusted, whereby it is possible to adjust the crimp ratio to the desired crimp ratio.

Further, examples of the method of weaving the weaving yarns YA and YB arranged in the same direction at different tensions during weaving include the following method. This method is a method that can be used without changing the type of yarn, and is a particularly suitable method from the viewpoint of uniformity of the woven fabric and the like.

When the weaving yarns YA and YB are warp yarns, at the time of weaving, they are preferably woven with increasing the tension of the warp yarn that is controlled to have the crimp ratio B (hereinafter also referred to as "the warp yarn having the crimp ratio B") and reducing the tension of the warp yarn that is controlled to have the crimp ratio A (hereinafter also referred to as "the warp yarn having the crimp ratio A") within a range that does not hinder the opening. For example, it is preferable that the tension of the warp yarn having the crimp ratio B is set to 0.5 to 1.5 cN/dtex and the tension of the warp yarn having the crimp ratio A is set to 0.05 to 0.3 cN/dtex.

Generally, in a high-density woven fabric, when the warp yarn tension is reduced during weaving in order to increase the crimp ratio of the warp yarn, it is difficult to increase the weft density by bumping (weft return). However, according to the above-described embodiment, the weft yarn can be restrained by the warp yarn having the crimp ratio A with the warp yarn having the crimp ratio B as a fulcrum, and bumping can be suppressed. Therefore, the crimp ratio of the warp yarn having the crimp ratio A can be increased.

Specific methods for adjusting the warp yarn tension within the above ranges include a method of adjusting a warp yarn feeding speed of a loom, and a method of adjusting a weft yarn driving speed. Whether the warp yarn tension actually falls within the above ranges during weaving can be confirmed, for example, by measuring a tension applied to each warp yarn with a tension measuring device in a center portion between a warp beam and a back roller during operation of the loom.

When it is desired to increase the crimp ratio A with respect to the crimp ratio B, the tension of the warp yarn having the crimp ratio A may be reduced with respect to the tension of the warp yarn having the crimp ratio B, and appropriately adjusted so as to obtain desired crimp ratios A and B. Specifically, it is preferable that the tension of the warp yarn having the crimp ratio B≥the tension of the warp yarn having the crimp ratio A×1.5 as long as there is no problem with the strength of the raw yarn.

Further, when the weaving yarns YA and YB are weft yarns, the tension when inserting the weft yarns between the warp openings may be adjusted.

Furthermore, examples of the method of weaving the weaving yarns arranged in the same direction at different tensions, while using the raw yarns Ya and Yb having different hot-water dimensional change rates, during weaving, include the following method.

As the raw yarns Ya and Yb used for the weaving yarns arranged in the same direction, it is preferable to select the raw yarns so that they have different hot-water dimensional change rates a and b, and a relationship thereof satisfies Formula 2.

$$b \geq a \times 1.1 \text{ (Formula 2)}$$

Then, when used as a warp yarn, the maximum one of the two or more types of hot-water dimensional change rates is taken as the "hot-water dimensional change rate b", and as the warp yarn that is controlled to have the crimp ratio B (hereinafter also referred to as the "warp yarn having the crimp ratio B") is woven with increasing the tension. In addition, the minimum one is taken as the "hot-water dimensional change rate a", and the warp yarn that is controlled to have the crimp ratio A (hereinafter also referred to as the "warp yarn having the crimp ratio A"), weaving is performed by reducing the tension within a range that does not hinder the opening. For example, it is preferable that the tension of the warp yarn having the crimp ratio B and the hot-water dimensional change rate b is set to 0.5 to 1.5 cN/dtex, and the tension of the warp yarn having the crimp ratio A and the hot-water dimensional change rate a is set to 0.05 to 0.3 cN/dtex. Specifically, it is preferable that the tension of the warp yarn having the crimp ratio B≥ the tension of the warp yarn having the crimp ratio A×1.5 as long as there is no problem with the strength of the raw yarn.

Although the woven structure of the woven fabric is a plain structure, it may be woven by passing a warp yarn and a weft yarn alternately up and down to be interlaced, and other than the plain-weave fabric woven by interlacing a warp yarn and a weft yarn one by one, as an applied structure, a vertically expanded structure in which several weft yarns are inserted at the same port, a horizontally expanded structure in which several adjacent warp yarns are formed in the same opening, or a woven fabric in which several warp yarns and weft yarns are arranged side by side like a basket weave may be used.

In addition, the loom used for producing the woven fabric is not particularly limited, and a water jet loom, an air jet loom, or a rapier loom can be used.

The woven fabric may be scoured, relaxed, preset, dyed and finished using conventional processing machines.

Moreover, when sea-island composite fibers are used, it is preferable to carry out sea removal treatment in the following step.

The sea-island composite fiber obtained by combining easily soluble sea component and island component is acid-treated to embrittle the sea component of the sea-island composite fiber. Examples of the acid include maleic acid. The treatment conditions are preferably a concentration of 0.1 to 1% by mass, a temperature of 100 to 150° C., and a time of 10 to 50 minutes.

Then, the sea component of the sea-island composite fiber, which has been embrittled by the acid treatment, is eluted by alkali treatment. Examples of the alkali include sodium hydroxide. The treatment conditions are preferably a concentration of 0.5 to 2% by mass, a temperature of 70 to 98° C., and a time of 60 to 100 minutes.

It is preferable that at least one surface of the woven fabric is calendered in order to achieve low air permeability or to obtain a thin plain-weave fabric. The calendering may be applied to only one side or both sides of the woven fabric. Further, the number of calendering is not particularly limited, and may be performed once or plural times as long as unevenness can be sufficiently compressed.

The calendering temperature is not particularly limited, but is preferably 80° C. or more higher and more preferably 120° C. or more higher than the glass transition temperature of the material used, and preferably 20° C. or more lower and more preferably 30° C. or more lower than the melting point of the material used. By setting the calendering temperature in the above ranges, a woven fabric capable of maintaining both low air permeability and high tear strength is obtained. On the other hand, when the calendering temperature is the glass transition temperature of the material used +80° C. or more, an appropriate degree of compression is obtained, and a woven fabric having low air permeability can be easily obtained. Also, when the calendering temperature is the melting point of the material used −20° C. or lower, an appropriate degree of compression is obtained, and the woven fabric has excellent tear strength.

For example, when polyamide is used as the material, the calendering temperature is preferably 120° C. to 200° C., and more preferably 130° C. to 190° C. In addition, when polyester is used as the material, the calendering temperature is preferably 160° C. to 240° C.

The calendering pressure is preferably 0.98 MPa (10 kgf/cm$^2$) or more, more preferably 1.96 MPa (20 kgf/cm$^2$) or more, and preferably 5.88 MPa (60 kgf/cm$^2$) or less, and more preferably 4.90 MPa (50 kgf/cm$^2$) or less. By setting the calendering pressure in the above ranges, a woven fabric capable of maintaining both low air permeability and tear strength is obtained. On the other hand, when the calendering pressure is 0.98 MPa (10 kgf/cm$^2$) or more, an appropriate degree of compression is obtained, and a woven fabric having excellent low air permeability is obtained. Further, when the calendering pressure is set to 5.88 MPa (60 kgf/cm$^2$) or less, the woven fabric is appropriately compressed, and the woven fabric has excellent tear strength.

Moreover, the material of the calendar roll is not particularly limited, but one roll is preferably made of metal. The metal roll can control its own temperature and can uniformly compress the surface of the material. The other roll is not particularly limited, but is preferably made of metal or resin, and when made of resin, it is preferably made of nylon.

It is preferable that at least one surface of the woven fabric is subjected to water repellent finishing, and various functional treatments and a soft finishing agent for adjusting texture and strength of the woven fabric can be used together.

A water repellent may be a general water repellent finishing agent for fibers, and for example, a silicone water repellent, a fluorine water repellent made of a polymer having a perfluoroalkyl group, and a paraffin water repellent are preferably used. Among them, the use of a fluorine water repellent is particularly preferable because the refractive index of a coating can be suppressed to a low level and reflection of light on the fiber surface can be reduced. As a method of water repellent finishing, a general method such as a padding method, a spray method, a printing method, a coating method or a gravure method can be used.

As the softening agent, amino-modified silicone, polyethylene-based, polyester-based, paraffin-based softening agent and the like can be used.

The plain-weave fabric thus obtained becomes a plain-weave fabric excellent in low air permeability and waterproofness, and can be usefully used for down wear, down jackets, sports clothing, futons, sleeping bags, umbrellas, medical base materials, or the like.

In addition, the plain-weave fabric of the present invention can also be used for medical applications. In particular, it is preferably used as a member of a prosthesis such as a stent graft, an artificial valve, an artificial blood vessel, an artificial dura mater or an artificial skin, or a patch repair material.

Among the above-mentioned prostheses, the plain-weave fabric of the present invention is particularly preferably used for a stent graft that is stored in a catheter and delivered to and placed in the affected area. The stent graft is placed in the aorta or the like in order to prevent the rupture of the aneurysm. However, if blood leaks from the graft portion made of a woven fabric, blood flow may flow into the aneurysm even after the placement, which may lead to rupture. The woven fabric of the present invention that is thin but has low water permeability and mechanical properties capable of adapting to the movement of a living body can be most effective when used for a stent graft.

Since the stent graft of the present invention is placed in a blood vessel and used in contact with blood, it is preferable that heparin, a heparin derivative or a low molecular weight heparin is carried on the surface of the graft substrate.

When heparin, a heparin derivative or a low molecular weight heparin is carried, the surface abundance can be quantified by X-ray electron spectroscopy (XPS), so that the effective surface amount can be known. When the amount of heparin carried is too large, hydrophilicity will increase and cell adhesion will become difficult, coating will be delayed, and it will not be stable. When the amount of heparin carried is too small, thrombus will be likely to form. Therefore, as the amount of heparin carried, when the abundance ratio of sulfur element contained in heparin is used as an index, the abundance ratio of sulfur element is preferably 3.0 atom % or more and 6.0 atom % or less.

As heparin, a heparin derivative or a low molecular weight heparin, reviparin, enoxaparin, parnaparin, certoparin, dalteparin and tinzaparin which are clinically used can be preferably used.

A method for carrying heparin, a heparin derivative or a low molecular weight heparin on the knitted fabric surface is not particularly limited, and known methods such as immobilization methods by covalently binding with a functional group introduced on the surface of a substrate (Japanese Patent No. 4152075, Japanese Patent No. 3497612, Japanese Translation of PCT International Application Publication No. H10-513074) and methods of immobilizing with a positively charged cationic compound introduced on the surface of a substrate by an ionic bond (Japanese Patent Publication No. S60-041947, Japanese Patent Publication No. S60-047287, Japanese Patent No. 4273965, Japanese Patent Laid-open Publication No. H10-151192) can be used. The sustained-release type surface support bound by binding heparin with an ionic bond is preferable in that it exhibits antithrombotic properties until it is covered by a neointima and does not inhibit the coverage by the neointima, and a method described in WO 2015/080177 is particularly preferably used.

EXAMPLES

Hereinafter, examples of the present invention will be described together with comparative examples.

The methods for measuring various characteristics used in this example are as follows.

(1) Total Fineness, Number of Filaments

The total fineness was measured based on JIS L 1013: 2010 8.3.1 (method A) (fineness based on corrected mass).

The number of filaments was measured based on JIS L 1013: 2010 8.4.

(2) Weaving Density

The weaving density was measured based on JIS L 1096: 2010 8.6.1.

A sample was placed on a flat table, and unnatural creases and tension were removed. The number of warp and weft yarns for 0.5 cm at 5 different points was counted, and respective average values thereof were calculated to convert to the number of yarns per 2.54 cm.

(3) Crimp Ratio

The crimp ratio was measured based on JIS L 1096:2010 8.7 (method B).

A sample was placed on a flat table, unnatural creases and tension were removed, and a mark was made at a distance of 200 mm for 3 different points at positions where yarns A1 and B1 with different crimp ratios are arranged adjacent to each other. A yarn between the marks was unraveled and used as unraveled yarn, a straightened length of the unraveled yarn under the initial load specified in JIS L1013, 5.1 was each measured, and the average value thereof was calculated to calculate a change length.

(4) Cover Factor

The cover factor (Cf) was calculated by the following equation.

$$Cf = N_W \times (D_W)^{1/2} + N_F \times (D_F)^{1/2}$$

$N_W$: Weaving density of warp yarns (yarns/2.54 cm)
$N_F$: Weaving density of weft yarns (yarns/2.54 cm)
$D_W$: Total fineness of warp yarns (dtex)
$D_F$: Total fineness of weft yarns (dtex)

(5) Air Permeability

The air permeability was measured based on JIS L 1096: 2010 8.26.1. (method A) (Frazier method).

(6) Water Pressure Resistance

The water pressure resistance was measured based on JIS L 1092: 2009 7.1.1 (method A) (low water pressure method).

(7) Hot-Water Dimensional Change Rate The hot-water dimensional change rate was measured based on JIS L 1013: 2010 8.18.1 (method B).

An initial load was applied to a sample, two points were marked at a distance of 500 mm, the initial load was removed, and the sample was immersed in hot water of 100° C. for 30 minutes. Thereafter, the sample was taken out, lightly drained with blotting paper or cloth, and air dried, then the initial load was applied again, the length between two points was each measured, the change length was calculated, and the average value of 5 times was rounded to one decimal place by JIS Z 8401 B (rounding method).

(8) Plain-Weave Fabric Thickness

According to JIS L 1096: 2010 8.4a), after waiting for 10 seconds under a pressure of 23.5 kPa to settle the thickness, the thickness was measured using a thickness measuring device for 5 different wall layers of a plain-weave fabric as a sample, and the average value was calculated.

(9) Tensile Mechanical Properties

Tensile mechanical properties were measured based on JIS L 1096 8.12.1 Method A (strip method) (1999). A sample of 5 cm in width and 30 cm in length with the warp direction of the woven fabric as the length direction was collected and extended at a tensile speed of 10 cm/min with a constant-speed extension type tensile tester with a gripping interval of 20 cm to measure breaking strength (N) and elongation at break (%). The results were plotted with the strength on the vertical axis and the elongation on the horizontal axis, and linear approximation by a least squares method in a section where the value obtained by dividing the elongation (%) by 100 is 0.00 to 0.03 (rounding off the third decimal place) was performed (Microsoft Excel), and modulus (Pa) was calculated by dividing the slope of the straight line by the cross-sectional area calculated from woven fabric thickness (mm) and sample width (mm). The measurement was performed for three samples, and the average value was obtained for each of the breaking strength, the elongation at break, and the tensile modulus.

(10) Water Permeability Rate

The plain-weave fabric was cut into 1 cm square sample pieces. Two pieces of punched doughnut-shaped packing having a diameter of 0.5 cm and a diameter of 3 cm were used to sandwich a 1 cm square plain-weave fabric sample so that liquid was not passed except the punched portion, and this plain-weave fabric sample was stored in a circular filtration filter housing. Reverse osmosis membrane filtered water at a temperature of 25° C. was passed through this circular filtration filter for 2 minutes or more until the sample piece sufficiently contained water. Under the conditions of a temperature of 25° C. and a filtration differential pressure of 120 mm Hg (1.6 kPa), total external pressure filtration of reverse osmosis membrane filtered water was performed for 30 seconds, and the permeation amount (mL) of water passing through a portion having a diameter of 1 cm was measured. The permeation amount was obtained by rounding off to the first decimal place, and the permeation amount (mL) was converted to a value per unit time (min) and effective area ($cm^2$) of the sample piece to measure water permeability performance at a pressure of 120 mm Hg (1.6 kPa). The measurement was performed for two samples, and the average value thereof was obtained.

(11) XPS Surface Elemental Analysis

The abundance ratio of sulfur atoms to the abundance of all atoms on the surface of the graft substrate can be determined by XPS.

[Measurement Conditions]

Device: ESCALAB 220iXL (manufactured by VG Scientific)

Excited X-ray: monochromatic AlKα1,2 ray (1486.6 eV)

X-Ray diameter: 1 mm

X Electron escape angle: 90° (detector tilt with respect to the surface of the antithrombotic material)

The graft substrate surface as used herein refers to a portion from the measurement surface up to a depth of 10 nm, detected when the X electron escape angle in the measurement conditions of XPS, that is, the detector tilt with respect to the graft substrate surface is measured as 90°. From the binding energy value of bound electrons in a substance to be obtained by irradiating the surface of the graft substrate with X-rays and measuring the energy of photoelectrons generated, atomic information of the surface of the graft substrate is obtained, and information on the valence and the binding state can be obtained from an energy shift of the peak of each binding energy value. Further, the area ratio of each peak can be used for quantification, that is, the abundance ratio of each atom, valence and binding state can be calculated.

Specifically, S2p peak indicating the presence of a sulfur atom has a binding energy value of around 161 eV to 170 eV, and in the present invention, it was found that the area ratio of the S2p peak to all the peaks is preferably 3.0 to 6.0 atom %, in that heparin bound to the surface of the stent graft exhibits antithrombotic properties without side effects. The abundance ratio of sulfur atoms to the abundance of all atoms was calculated by rounding off the second decimal place.

Example 1

A polyethylene terephthalate fiber of 56 dtex, 18 filaments and a hot-water dimensional change rate (a1) of 7.9% as an raw yarn of weaving yarn (A1) having crimp ratio A, and a polyethylene terephthalate fiber of 56 dtex, 18 filaments and a hot-water dimensional change rate (b1) of 28.5% as an raw yarn of weaving yarn (B1) having crimp ratio B were used for a warp yarn. Further, a polyethylene terephthalate fiber of 56 dtex, 18 filaments and a hot-water dimensional change rate (a1) of 7.9% as an raw yarn was used for a weft yarn. The relationship between hot-water dimensional change rates a1 and b1 in this example is "b1=a1×3.6".

Then, at the time of weaving, the tension of yarn A1 and yarn B1 was set to 0.5 cN/dtex, the warp density was set to 175 yarns/2.54 cm, and the weft density was set to 100 yarns/2.54 cm, and a plain-weave fabric was obtained by weaving with a plain weave structure in which one warp yarn and one weft yarn were interlaced. The obtained plain-weave fabric was scoured using an open soaper, pre-set at 185° C.×30 sec using a pin tenter, and intermediate set at 180° C.×30 sec. Thereafter, the woven fabric was calendered (processing conditions: cylinder processing, temperature 170° C., pressure 2.45 MPa (25 kgf/$cm^2$, speed 20 m/min) on one side twice to obtain a plain-weave fabric with a warp density of 180 yarns/2.54 cm, a weft density of 175 yarns/2.54 cm, and a cover factor of 2655. The obtained plain-weave fabric was evaluated for air permeability, water pressure resistance, thickness, tensile mechanical properties and water permeability rate by the above-mentioned method.

The properties of the obtained plain-weave fabric are shown in Table 1.

Example 2

As yarn (A1) having crimp ratio A and yarn (B1) having crimp ratio B, a polyethylene terephthalate of 56 dtex, 18 filaments and a hot-water dimensional change rate (a1) of 7.9% was used for a warp yarn. Further, a polyethylene terephthalate fiber of 56 dtex, 18 filaments and a hot-water dimensional change rate (a1) of 7.9% was used for a weft yarn.

Then, at the time of weaving, the yarn A1 and the yarn B1 were alternately arranged one by one at a ratio of 1:1 (number ratio), the tension of yarn B1 was set to 0.6 cN/dtex, the tension of yarn A1 was set to 0.1 cN/dtex, the warp density was set to 190 yarns/2.54 cm, and the weft density was set to 185 yarns/2.54 cm, and a plain-weave fabric was obtained by weaving with a plain weave structure in which one warp yarn and one weft yarn were interlaced. The obtained plain-weave fabric was scoured using an open soaper, pre-set at 185° C.×30 sec using a pin tenter, and intermediate set at 180° C.×30 sec. Thereafter, the woven fabric was calendered (processing conditions: cylinder processing, temperature 170° C., pressure 2.45 MPa (25 kgf/$cm^2$, speed 20 m/min) on one side twice to obtain a plain-weave fabric with a warp density of 198 yarns/2.54 cm, a weft density of 190 yarns/2.54 cm, and a cover factor of 2902. The obtained plain-weave fabric was evaluated for air permeability, water pressure resistance, thickness, tensile mechanical properties and water permeability rate by the above-mentioned method.

The properties of the obtained plain-weave fabric are shown in Table 1.

Example 3

A polyethylene terephthalate fiber of 56 dtex, 18 filaments and a hot-water dimensional change rate (a1) of 7.9% as an raw yarn of weaving yarn (A1) having crimp ratio A, and a polyethylene terephthalate fiber of 56 dtex, 18 filaments and a hot-water dimensional change rate (b1) of 28.5% as an raw yarn of weaving yarn (B1) having crimp ratio B were used for a warp yarn. Further, a polyethylene terephthalate fiber of 56 dtex, 18 filaments and a hot-water dimensional change rate (a1) of 7.9% as an raw yarn was used for a weft yarn. The relationship between hot-water dimensional change rates a1 and b1 in this example is "b1=a1×3.6".

Then, at the time of weaving, the yarn A1 and the yarn B1 were alternately arranged one by one at a ratio of 1:1 (number ratio), the tension of yarn B1 was set to 0.6 cN/dtex, the tension of yarn A1 was set to 0.1 cN/dtex, the warp density was set to 200 yarns/2.54 cm, and the weft density was set to 195 yarns/2.54 cm, and a plain-weave fabric was obtained by weaving with a plain weave structure in which one warp yarn and one weft yarn were interlaced. The obtained plain-weave fabric was scoured using an open soaper, pre-set at 185° C.×30 sec using a pin tenter, and intermediate set at 180° C.×30 sec. Thereafter, the woven fabric was calendered (processing conditions: cylinder processing, temperature 170° C., pressure 2.45 MPa (25 kgf/cm$^2$, speed 20 m/min) on one side twice to obtain a plain-weave fabric with a warp density of 210 yarns/2.54 cm, a weft density of 203 yarns/2.54 cm, and a cover factor of 3089. The obtained plain-weave fabric was evaluated for air permeability, water pressure resistance, thickness, tensile mechanical properties and water permeability rate by the above-mentioned method.

The properties of the obtained plain-weave fabric are shown in Table 1.

Example 4

As yarn (A1) having crimp ratio A and yarn (B1) having crimp ratio B, a polyethylene terephthalate (sea-island composite fiber) of 44 dtex, 9 filaments and a hot-water dimensional change rate (a1) of 7.4% was used for a warp yarn. Further, a polyethylene terephthalate fiber (sea-island composite fiber) of 44 dtex, 9 filaments and a hot-water dimensional change rate (a1) of 7.4% was used for a weft yarn.

Then, at the time of weaving, the yarn A1 and the yarn B1 were alternately arranged one by one at a ratio of 1:1 (number ratio), the tension of yarn B1 was set to 0.6 cN/dtex, the tension of yarn A1was set to 0.1 cN/dtex, the warp density was set to 215 yarns/2.54 cm, and the weft density was set to 200 yarns/2.54 cm, and a plain-weave fabric was obtained by weaving with a plain weave structure in which one warp yarn and one weft yarn were interlaced. The obtained plain-weave fabric was scoured using an open soaper, and then subjected to sea removal treatment. Maleic acid was used as an acid, and the treatment conditions were a concentration of 0.2% by mass, a temperature of 130° C., and a time of 30 minutes. Sodium hydroxide was used as an alkali, and the treatment conditions were a concentration of 1% by mass, a temperature of 80° C., and a time of 90 minutes. The fineness of the weaving yarn after the sea removal treatment was both 35.2 dtex and 630 filaments. Thereafter, the woven fabric was calendered (processing conditions: cylinder processing, temperature 170° C., pressure 2.45 MPa (25 kgf/cm$^2$, speed 20 m/min) on one side twice to obtain a plain-weave fabric with a warp density of 238 yarns/2.54 cm, a weft density of 230 yarns/2.54 cm, and a cover factor of 2775. The obtained plain-weave fabric was evaluated for air permeability, water pressure resistance, thickness, tensile mechanical properties and water permeability rate by the above-mentioned method.

Figure 2:
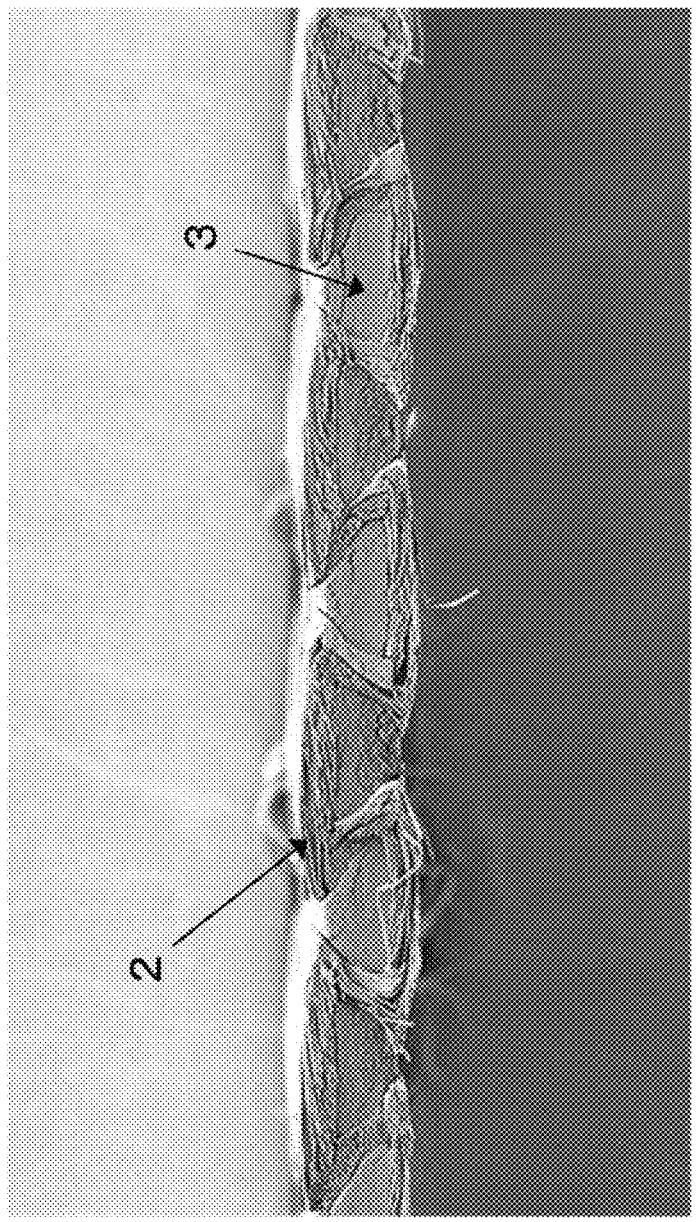
FIG. 2 is an SEM photograph of a cross section of a weft yarn when cut along cutting line $\alpha$ in the warp direction of crimp ratio A in FIG. 1.
Figure 3:
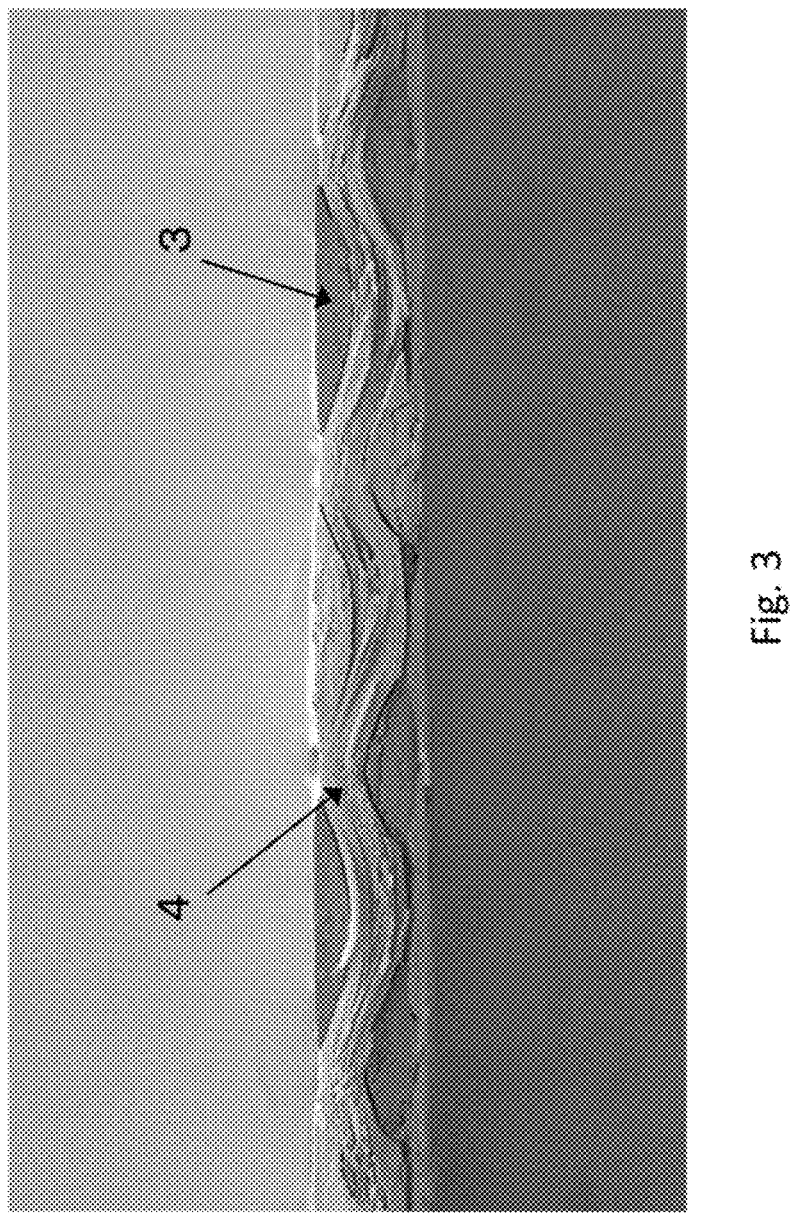
FIG. 3 is an SEM photograph of a cross section of a weft yarn when cut along cutting line $\beta$ in the warp direction of crimp ratio B in FIG. 1.

The properties of the obtained plain-weave fabric are shown in Table 1 and FIGS. 1, 2 and 3. Further, a surface scanning electron microscope (SEM) photograph of the obtained plain-weave fabric was shown in FIG. 1, an SEM photograph of a cross section of the weft yarn when cut along cutting line α in the warp direction of the crimp ratio A in FIG. 1 was shown in FIG. 2, and an SEM photograph of a cross section of the weft yarn when cut along the cutting line β in the warp direction of the crimp ratio B in FIG. 1 was shown in FIG. 3.

FIG. 2 shows that in the calendered plain-weave fabric 1, the surface of the weft yarn located on the calendering side is covered with warp yarn 2 with the crimp ratio A that is compressed and spread by calendering from the left and right to form a dense structure. FIG. 3 shows that warp 4 having the crimp ratio B is more closely interwoven with the crimp ratio smaller than the weft yarn 3 and the warp yarn 2 having the crimp ratio A.

Example 5

The woven fabric obtained in Example 4 was subjected to antithrombotic treatment. The woven fabric was immersed in an aqueous solution of 5.0% by weight potassium permanganate (manufactured by Wako Pure Chemical Industries, Ltd.) and 0.6 mol/L sulfuric acid (manufactured by Wako Pure Chemical Industries, Ltd.), and reacted at 60° C. for 3 hours to hydrolyze and oxidize PET mesh. The aqueous solution after the reaction was removed, and the woven fabric was washed with hydrochloric acid (Wako Pure Chemical Industries, Ltd.) and distilled water.

The woven fabric was then immersed in an aqueous solution of 0.5% by weight DMT-MM (manufactured by Wako Pure Chemical Industries, Ltd.) and 5.0% by weight PEI (LUPASOL (registered trademark) P; manufactured by BASF SE), and reacted at 30° C. for 2 hours, so that the PEI was covalently bound to the woven fabric by a condensation reaction. The aqueous solution after the reaction was removed, and the woven fabric was washed with distilled water.

Further, the woven fabric was immersed in a 1% by weight aqueous solution of ethyl bromide (manufactured by Wako Pure Chemical Industries, Ltd.) in methanol, reacted at 35° C. for 1 hour, then heated to 50° C. and reacted for 4 hours, so that the PEI covalently bound to the surface of the PET mesh was turned into quaternary ammonium. The aqueous solution after the reaction was removed, and the woven fabric was washed with methanol and distilled water.

Finally, it was immersed in an aqueous solution (pH=4) of 0.75% by weight sodium heparin (manufactured by Organon API) and 0.1 mol/L sodium chloride and reacted at 70° C. for 6 hours to ionically bond with the PEI. The aqueous solution after the reaction was removed, and the woven fabric was washed with distilled water.

The abundance ratio of sulfur atoms to the abundance of all atoms on the surface of the graft substrate, determined by XPS, was 4.7%.

The woven fabric cut into a 95 mm×300 mm strip was rolled into a cylinder so that the length of 300 mm was in the long axis direction, and the ends are sewn together to create a graft substrate, and a φ5 mm nickel titanium alloy ring was sewn thereto to create a stent graft.

A 3 cm long portion was cut out from the stent graft and connected to a silicon tube to create a circulation circuit. The circulation circuit was filled with pig blood and circulated at 200 mL/min for 10 minutes. After 10 minutes, an inner wall of the stent graft removed from the circuit was rinsed and then dried under reduced pressure. The same operation was also performed on an untreated stent graft. As a result of quantifying the amount of adhered thrombus as an increase in dry weight before and after blood circulation, weight increases of heparin-treated stent graft and untreated graft were 50 mg and 450 mg, respectively, in which the amount of adhered thrombus was clearly small in the heparin-treated.

Comparative Example 1

A polyethylene terephthalate fiber of 56 dtex, 18 filaments and a hot-water dimensional change rate (a1) of 7.9% was used for warp and weft yarns.

Then, at the time of weaving, the tension of warp yarn was set to 0.5 cN/dtex, the warp density was set to 175 yarns/2.54 cm, and the weft density was set to 100 yarns/2.54 cm, and a plain-weave fabric was obtained by weaving with a plain weave structure in which one warp yarn and one weft yarn were interlaced. The obtained plain-weave fabric was scoured using an open soaper, pre-set at 185° C.×30 sec using a pin tenter, and intermediate set at 180° C.×30 sec. Thereafter, the woven fabric was calendered (processing conditions: cylinder processing, temperature 170° C., pressure 2.45 MPa (25 kgf/cm², speed 20 m/min) on one side twice to obtain a plain-weave fabric with a warp density of 180 yarns/2.54 cm, a weft density of 107 yarns/2.54 cm, and a cover factor of 2146. The obtained plain-weave fabric was evaluated for air permeability, water pressure resistance, thickness, tensile mechanical properties and water permeability rate by the above-mentioned method.

The properties of the obtained plain-weave fabric are shown in Table 1. Although the thickness was thin, the breaking strength/elongation, modulus, and water permeability were insufficient for use in a stent graft.

Comparative Example 2

As yarn (A1) having crimp ratio A and yarn (B1) having crimp ratio B, a polyethylene terephthalate of 56 dtex, 18 filaments and a hot-water dimensional change rate (a1) of 7.9% was used for a warp yarn. Further, a polyethylene terephthalate fiber of 56 dtex, 18 filaments and a hot-water dimensional change rate (a1) of 7.9% was used for a weft yarn.

Then, at the time of weaving, the yarn A1 and the yarn B1 were alternately arranged one by one at a ratio of 1:1 (number ratio), the tension of yarn B1 was set to 0.7 cN/dtex, the tension of yarn A1 was set to 0.4 cN/dtex, the warp density was set to 175 yarns/2.54 cm, and the weft density was set to 100 yarns/2.54 cm, and a plain-weave fabric was obtained by weaving with a plain weave structure in which one warp yarn and one weft yarn were interlaced. The obtained plain-weave fabric was scoured using an open soaper, pre-set at 185° C.×30 sec using a pin tenter, and intermediate set at 180° C.×30 sec. Thereafter, the woven fabric was calendered (processing conditions: cylinder processing, temperature 170° C., pressure 2.45 MPa (25 kgf/cm², speed 20 m/min) on one side twice to obtain a plain-weave fabric with a warp density of 178 yarns/2.54 cm, a weft density of 104 yarns/2.54 cm, and a cover factor of 2109. The obtained plain-weave fabric was evaluated for air permeability, water pressure resistance, thickness, tensile mechanical properties and water permeability rate by the above-mentioned method.

The properties of the obtained plain-weave fabric are shown in Table 1. Although the thickness was thin, the breaking strength/elongation, modulus, and water permeability were insufficient for use in a stent graft.

TABLE 1

| | | Example 1 | Example 2 | Example 3 | Example 4 | Comparative Example 1 | Comparative Example 2 |
|---|---|---|---|---|---|---|---|
| Total fineness of warp yarn A1 | dtex | 56 | 56 | 56 | 44 | 56 | 56 |
| Number of filaments of warp yarn A1 | f | 18 | 18 | 18 | 9 | 18 | 18 |
| Total fineness of warp yarn A1 after sea removal | dtex | — | — | — | 35.2 | — | — |
| Number of filaments of warp yarn A1 after sea removal | f | — | — | — | 630 | — | — |
| Hot-water dimensional change rate a1 | % | 7.9 | 7.9 | 7.9 | 7.4 | 7.9 | 7.9 |
| Tension of warp yarn A1 during weaving | cN/dtex | 0.5 | 0.1 | 0.1 | 0.1 | 0.5 | 0.4 |
| Total fineness of warp yarn B1 | dtex | 56 | 56 | 56 | 44 | 56 | 56 |
| Number of filaments of warp yarn B1 | f | 18 | 18 | 18 | 9 | 18 | 18 |
| Total fineness of warp yarn B1 after sea removal | dtex | — | — | — | 35.2 | — | — |
| Number of filaments of warp yarn B1 after sea removal | f | — | — | — | 630 | — | — |
| Hot-water dimensional change rate b1 | % | 28.5 | — | 28.5 | — | — | — |
| Tension of warp yarn B1 during weaving | cN/dtex | 0.5 | 0.6 | 0.6 | 0.6 | — | 0.7 |
| Finishing density of warp yarn | yarns/2.54 cm | 180 | 198 | 210 | 238 | 180 | 178 |
| Total fineness of weft yarn | dtex | 56 | 56 | 56 | 44 | 56 | 56 |
| Number of filaments of weft yarn | f | 18 | 18 | 18 | 9 | 18 | 18 |
| Total fineness of weft yarn after sea removal | dtex | — | — | — | 35.2 | — | — |

TABLE 1-continued

| | | Example 1 | Example 2 | Example 3 | Example 4 | Comparative Example 1 | Comparative Example 2 |
|---|---|---|---|---|---|---|---|
| Number of filaments of weft yarn after sea removal | f | — | — | — | 630 | — | — |
| Hot-water dimensional change rate of weft yarn | % | 7.9 | 7.9 | 7.9 | 7.4 | 7.9 | 7.9 |
| Finishing density of weft yarn | yarns/2.54 cm | 175 | 190 | 203 | 230 | 107 | 104 |
| Cover factor | — | 2655 | 2902 | 3089 | 2775 | 2146 | 2109 |
| Crimp ratio A | % | 74.2 | 104.8 | 134.5 | 105.2 | 6.3 | 14.4 |
| Crimp ratio B | % | 5.6 | 5.8 | 4.3 | 5.6 | 5.8 | 3.4 |
| Crimp ratio A/Crimp ratio B | | 13.3 | 18.1 | 31.3 | 18.8 | 1.1 | 4.2 |
| Air permeability | $cm^3/cm^2 \cdot sec$ | 0.06 | 0.05 | 0.03 | 0.05 | 1.12 | 1.46 |
| Water pressure resistance | kPa | 29.4 | 31.4 | 33.4 | 30.2 | 3.9 | 4.3 |
| Thickness | μm | 67 | 67 | 68 | 62 | 42 | 39 |
| Tensile strength at break | N/cm | 224.5 | 249.8 | 261.2 | 211.7 | 165.9 | 147.8 |
| Tensile elongation at break | % | 50.4 | 46.4 | 42.9 | 49.1 | 56.3 | 57.7 |
| Tensile elastic modulus | Pa | 350 | 420 | 475 | 337 | 290.8 | 282.2 |
| Water permeability rate | $mL/min/cm^2$ | 5.0 | 0.5 | 0.1 | 13.0 | 87.9 | 113.0 |

DESCRIPTION OF REFERENCE SIGNS

1: Plain-weave fabric
2: Warp yarn having crimp ratio A
3: Weft yarn
4: Warp yarn having crimp ratio B
α: Cutting line in warp direction of crimp ratio A
β: Cutting line in warp direction of crimp ratio B

The invention claimed is:

1. A plain-weave fabric woven by interlacing weaving yarns in warp and weft, wherein weaving yarns YA and YB arranged in the same direction have different crimp ratios A and B, respectively, a relationship thereof satisfies the following Formula 1, the crimp ratio A is 30% or more, and the crimp ratio B is 4% or more; A≥B×1.2 (Formula 1).

2. The plain-weave fabric according to claim 1, wherein the weaving yarn YA having the crimp ratio A and the weaving yarn YB having the crimp ratio B are arranged at a ratio of 1:1.

3. The plain-weave fabric according to claim 1, having a cover factor of 2400 or more.

4. The plain-weave fabric according to claim 1, having an air permeability of 0.1 $cm^3/cm^2 \cdot sec$ or less.

5. The plain-weave fabric according to claim 1, having a water pressure resistance of 9.8 kPa (1000 $mmH_2O$) or more.

6. The plain-weave fabric according to claim 1, wherein at least one surface is calendered.

7. The plain-weave fabric according to claim 1, wherein at least one surface is subjected to water repellent finishing.

8. The plain-weave fabric according to claim 1, wherein the weaving yarns YA and YB arranged in the same direction have different hot-water dimensional change rates a and b, respectively, and are weaving yarns woven using raw yarns Ya and Yb in which a relationship thereof satisfies the following Formula 2; b≥a×1.1 (Formula 2).

9. The plain-weave fabric according to claim 1, having a tensile strength at break in the warp direction of 200 N/cm or more.

10. The plain-weave fabric according to claim 1, having a tensile elongation at break in the warp direction of 40% or more and 55% or less.

11. The plain-weave fabric according to claim 1, having a tensile modulus in the warp direction of 300 Pa or more.

12. The plain-weave fabric according to claim 1, having a water permeability rate of 70 $mL/min/cm^2$ or less.

13. The plain-weave fabric according to claim 1, which is used for a prosthesis.

14. The plain-weave fabric according to claim 1, which is used for a stent graft.

15. A stent graft comprising the plain-weave fabric according to claim 1 as a graft substrate.

16. The stent graft according to claim 15, which carries heparin, a heparin derivative, or a low molecular weight heparin.

* * * * *